United States Patent [19]

Murray et al.

[11] 4,016,606
[45] Apr. 12, 1977

[54] KNEE JOINT PROSTHESIS

[75] Inventors: David George Murray; James Henry Somerset, both of Syracuse, N.Y.

[73] Assignee: Research Corporation, New York, N.Y.

[22] Filed: July 14, 1975

[21] Appl. No.: 595,739

[52] U.S. Cl. .............................. 3/1.911; 128/92 C
[51] Int. Cl.² .......................................... A61F 1/24
[58] Field of Search .................. 3/1, 1.9–1.913; 128/92 C

[56] References Cited

UNITED STATES PATENTS

| 3,694,821 | 10/1972 | Moritz | 3/1.911 |
| 3,696,446 | 10/1972 | Bousquet et al. | 3/1.911 |
| 3,748,662 | 7/1973 | Helfet | 3/1.911 |
| 3,868,730 | 3/1975 | Kaufer et al. | 3/1 |
| 3,924,277 | 12/1975 | Freeman et al. | 3/1.911 |

Primary Examiner—Ronald L. Frinks
Attorney, Agent, or Firm—Cameron, Kerkam, Sutton, Stowell & Stowell

[57] ABSTRACT

A knee joint prosthesis comprises a tibial component adapted to be received on the upper end of the tibia, a tibial insert having a generally planar table portion and a spheroidal center depression carried by the tibial component and a femoral component adapted to be received on the lower end of the femur, the femoral component includes a portion having a depending generally spheroidal surface which cooperates with the spheroidal depression in the tibial insert.

8 Claims, 10 Drawing Figures

FIG. 5.
FIG. 6.
FIG. 8.
FIG. 7.
FIG. 9.
FIG. 10.
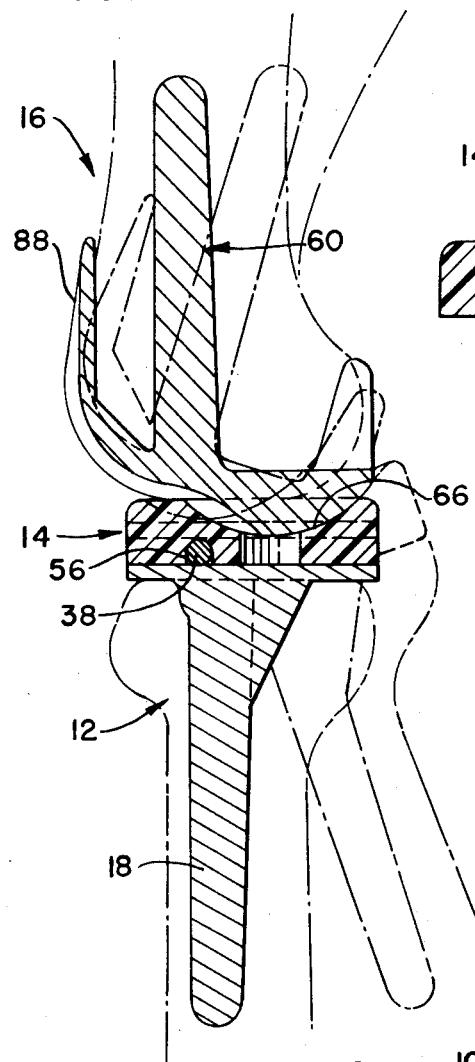
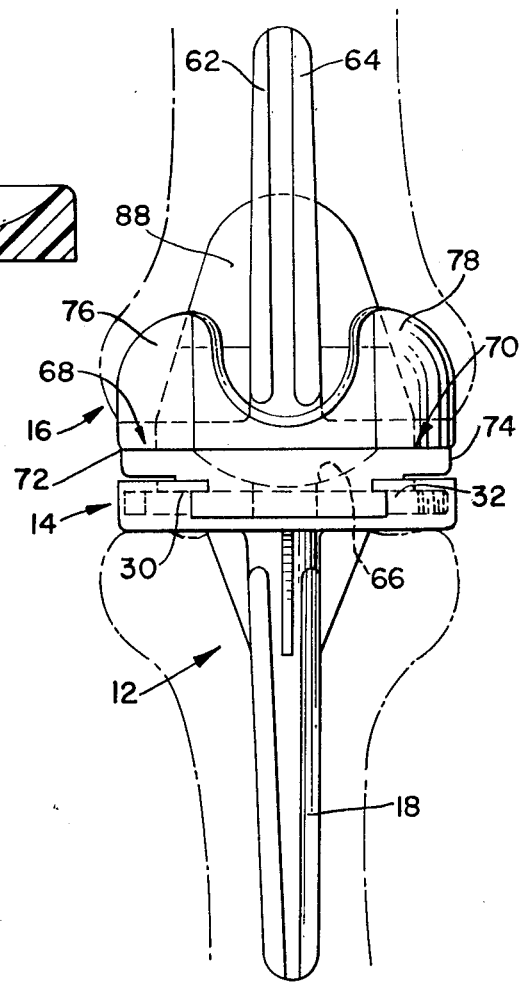
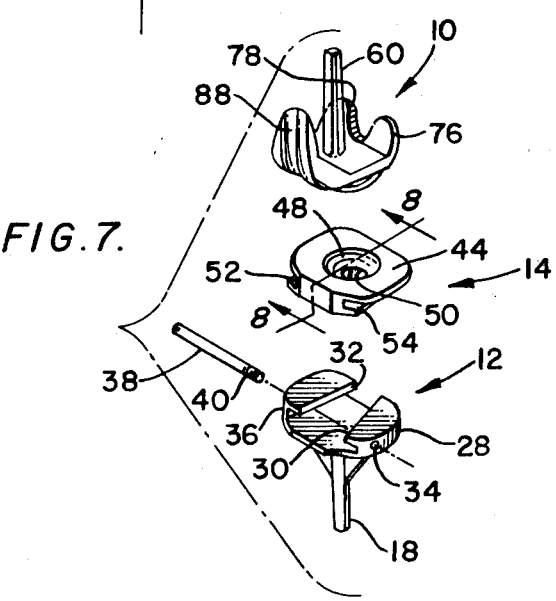
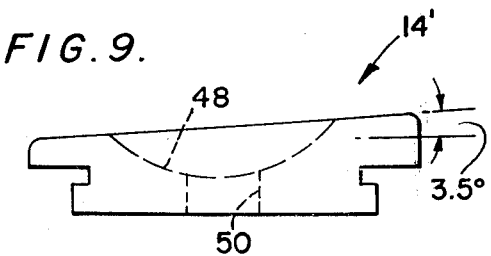
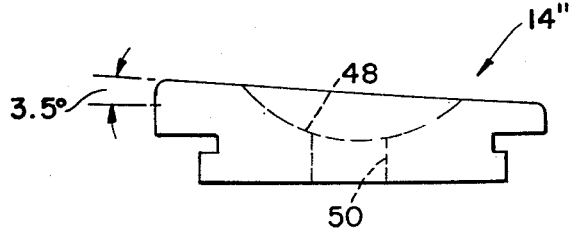

KNEE JOINT PROSTHESIS

This invention is directed to a knee joint prosthesis which is designed to fulfill a number of criteria which are generally lacking in prior art prostheses.

The motion of the human knee joint is complicated. It is known that the principal motion of the tibia is a flexion exhibiting an angular velocity about an axis which is perpendicular to the sagittal plane. Simultaneously, the tibia exhibits an angular velocity, having components perpendicular to the flexion component.

It is an object of the invention to provide a prosthesis which will permit those essential components of tibial rotation which allow proper knee function and which preclude the transmission of unnatural constraint forces through the joint. The motion provided by the joint described and claimed herein is motion around a fixed point with limitations on motion in the lateral direction. The prosthesis is constructed so that no restriction is placed on the essential rotations of the tibia, viz: angular velocity perpendicular to the sagittal plane and angular velocity of the tibia parallel to the tibial axis.

It is another object of the invention to provide a knee joint prosthesis designed to permit rotation at the joint about a longitudinal axis unrestricted by the elements of the prosthesis itself.

A further object is to provide such a prosthesis wherein the stem design thereof allows firm fixation of a pair of the components of the prosthesis into bone with the addition of cement.

A further object is to provide a knee joint prosthesis wherein one of the components comprises a detachable insert which permits correction of deformities of the patient or correction for ligament laxity at the time of the operation and after all major components are cemented firmly into the bone of the receiver.

A further object is to provide a knee joint prosthesis including a detachable insert whereby the prosthesis may be relatively simply revised should such revision be indicated at a later date.

A further object is to provide a prosthesis including a forwardly and upwardly directed flange which protects the patella or knee cap from rubbing on raw bone and provides for the incorporation of a knee cap prosthesis if one is indicated.

A further object is to provide a knee joint prosthesis which provides stability in a horizontal plane to thereby prevent displacement of the tibia in respect to the femur.

These and other objects and advantageous are provided by the prosthesis of the present invention as described in the specification and claims, wherein the terms "front," "rear," "left," "right," "up" and "down" are directions oriented in respect to a patient having the prosthesis.

In general the invention may be defined as a knee joint prosthesis comprising a tibial component; a tibial component insert; and a femoral component; the tibial component comprising an anchoring stem portion, one end of the stem portion adapted to the received in a longitudinal bore in a patient's tibia, the other end of the stem portion being integral with a table, the top surface of which is generally normal to the stem portion and having lateral edge flanges;

the tibial component insert comprising a plate shaped to be received on the tibial component table in locking engagement with the table edge flanges and the upper surface thereof having a centrally positioned spheroidal depression surrounded by a plane surface;

the femoral component comprising a stem, one end of the stem adapted to be received in a longitudinal bore in a patient's femur, the other end of the stem being integral with a depending generally spheroidal surface having generally the same radius as the radius of the spheroidal depression in the insert, the spheroidal surface further having lateral shoulders each of which has a flat surface which engages the plane surface of the insert when the stems of the tibial and femoral components are in longitudinal alignment and a cylindrical surface having a radius of curvature about the axis of pivotal motion of the spheroidal surface to permit rearward swing motion of the tibial component relative to the femoral component and rotation of said components normal to the longitudinal axes of the stems.

The invention will be more particulary described with reference to the accompanying drawings wherein;

FIG. 5 is a longitudinal sectional view similar to that illustrated in FIG. 2 showing two positions of the components of the prosthesis of the invention;

FIG. 6 is a rear elevational view of the structures shown in FIGS. 1–5;

FIG. 7 is an exploded perspective view of a form of the prosthesis of the invention.

FIG. 8 is a sectional view through the tibial insert component of the prosthesis;

FIG. 9 is an end view of a modified form of tibial component insert; and

FIG. 10 is a view like FIG. 9 of a further modified form of tibial component insert.

Figure 1:
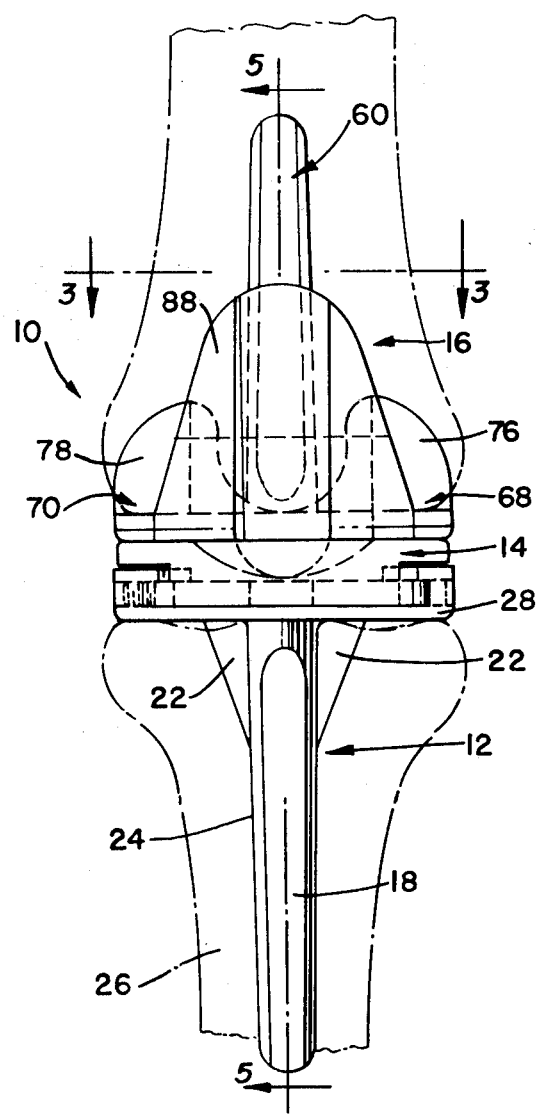
FIG. 1 is a front elevational view of an embodiment of the present invention showing in broken lines a femur and tibia of a patient.

Referring to the drawings, 10 generally designates an embodiment of the present knee joint prosthesis and includes a tibial component 12, a tibial component insert 14 and femoral component 16.

The tibial component and the femoral component are generally composed of metal and any suitable generally inert metal or alloy may be employed in their construction. Cobalt-chromium base alloys such as Vitallium comprising Chromium — 25–30%
Nickel + Iron less than 1%
Molybdenum — 5–7%
Carbon — 0.35% maximum
Manganese — 1% maximum
Magnesium — 1% maximum
Silicon — 1% maximum
Boron — 0.007% maximum and the remainder cobalt has been found to provide satisfactory results.

The tibial component 12 includes an anchoring stem 18 fluted on two sides as indicated at 20 and provided with strengthening and anchoring webs shown at 22 so that when a bore indicated at 24 is made in the patient's tibia 26 and a cement such as methyl methacrylate adhesive is employed to bond the stem within the bore a very satisfactory joining of the tibial component to the tibia is provided. For an average adult patient a stem of a length of about 3½ inches has provided very satisfactory results.

The upper end of the stem portion 18 is integrally formed with a table or platform 28 which has an upper surface normal to the stem 18. The table or top surface portion 28 is provided with a pair of edge flanges 30 and 32 which in the illustrated form of the invention are tapered inwardly from the front to the rear as more clearly shown in the perspective view, FIG. 7 of the drawing.

Further, a bore is provided as at 34 and 36 in each of the top flanges which bores are adapted to receive a locking pin 38 threaded as at 40 to mate with internal threads in bore 34 as to be more fully described hereinafter.

The tibial component insert generally designated 14 is composed of a plastic such as a high impact or high density polyethylene. The insert generally has a flat or planar upper surface 44 which surrounds a centrally disposed spherical depression 48. The center of the depression may be removed as at 50 to provide a pocket to receive any debris, such as small fragments of polyethylene abraded from the spherical depression in the insert following the implantation of the prosthesis.

Further, by removing the center of the spherical depression assures that the mating surfaces between the femoral part and the insert occurs along a circle within the annulus. This configuration allows a dimensional tolerance on the radius of the femoral sphere yet guarantees contact between the mating spherical surfces within the annulus.

Further, as more clearly illustrated in, for example, FIG. 7, the tibial component insert is inleted or grooved as at 52 and 54 in a cooperating manner to the edge flanges 30 and 32 of the table portion 28 of the tibial component 12 whereby the tibial insert may be simply slid into a tight sealing engagement with the tibial component following anchoring of the tibial and femoral components to their respective bones and then locked in such position by means of the pin 38 passing through the bore or opening 56 shown, for example, in FIGS. 5 and 8 of the drawings.

The front to rear inward taper of the edge flanges 30 and 32 of the table of the tibial component 12 and the cooperating grooves 52 and 54 of the insert and uniquely suited for the knee joint prothesis as when the leg is fully extended the resultant of the force applied to the prosthesis by the femur is not exactly vertical but is rather inclined slightly rearwardly, producing a small horizontal component of force to the spherical socket which is rearwardly directed. Thus, instead of relying solely on the pin 38 to hold the insert in place and resist this horizontal force, the tapered arrangement resists the insert's displacement, in the posterior direction, and would do so even in the absence of the pin.

The femoral component comprises a stem portion 60 which like the stem portion 18 of the tibial component is fluted along two faces as at 62 and 64 to assist in rigid anchoring of the femoral component to the femur. The lower end of the stem is integral with a depending generally spheroidal projection or surface 66. The radius of curvature of the spheroidal surface 66 is the same as the radius of the spheroidal depression 48 in the tibial insert member 14 so that these two surfaces, when in operative alignment, prevent lateral displacement of the two components without limiting the axial rotation of one component relative to the other or rocking motion of on component relative to the other.

In order to restrict rocking or pivotal motion between the depending spherical surface 66 on the femoral component and the spherical depression on the tibial insert, the spherical surface 66 of the femoral component is bounded on its two lateral sides with a pair of shoulders generally designated 68 and 70. When the tibial and femoral components are vertically aligned, a generally plane surface designated 72 for shoulder 68 and 74 for shoulder 70 stabilizes the prosthesis when the leg is in the extended position. Each of the flat or generally flat surfaces on the pair of shoulders is followed, in the rearward direction, by cylindrical portions 76 for shoulder 68 and 78 for shoulder 70. Each of the cylindrical portions 76 and 78 has a radius of curvature which permits pivotal motion of the spheroidal surface 66 in the spheroidal depression 48 to thereby permit the lower leg to pivot rearwardly. The forward portions of the shoulders which include the flange 88 are curved. The radii of curvature thereof differs from that of the cylindrical portions 76 and 78 thereby reducing the tendency for the lower leg to move forwardly from the extended position in relation to the upper leg. The shaped flange 88 provides a zone of contact for the patient's patella or knee cap and prevents the knee cap from rubbing on raw bone.

The prosthesis of the invention is not "handed," that is, while the prosthesis is made in several different sizes to adapt to the patient's size, a prosthesis will fit either the left or right knee.

Figure 2:
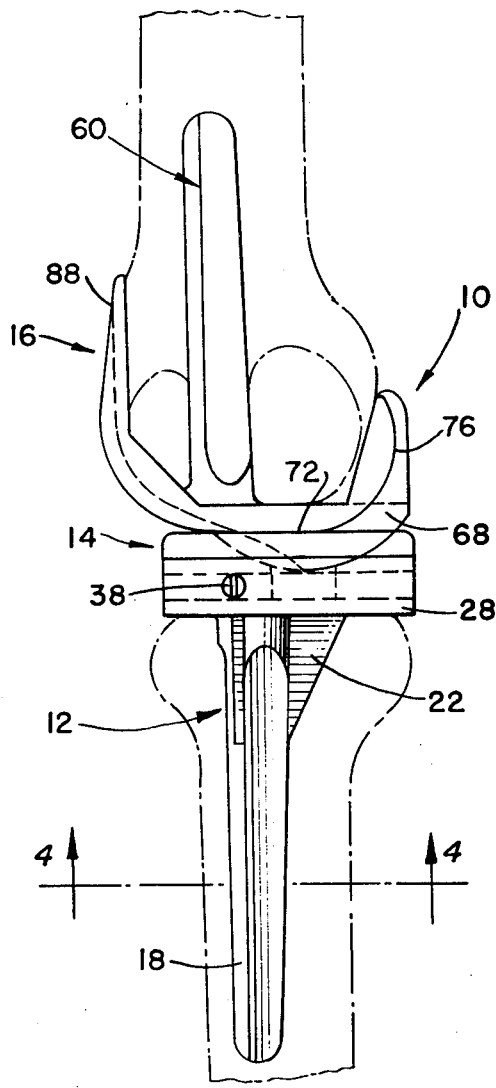
FIG. 2 is a side elevational view of the structures shown in FIG. 1.
Figure 3:
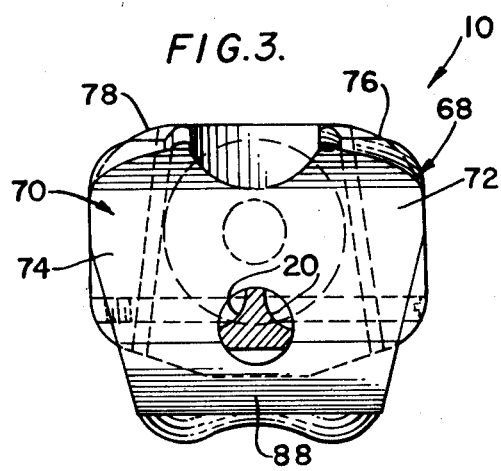
FIG. 3 is a section on line 3—3 of FIG. 1.
Figure 4:
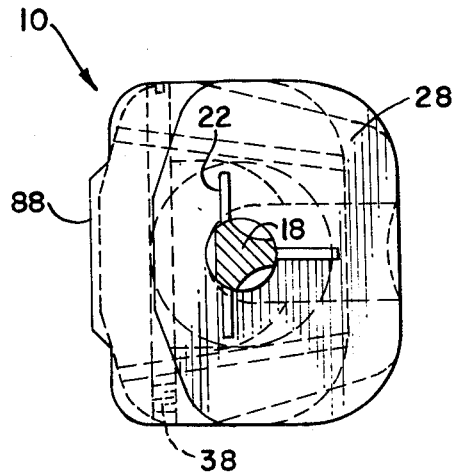
FIG. 4 is a section on line 4—4 of FIG. 2.

In addition to size variations of the prosthesis for different size patients, the tibial insert 14 is made both in a standard form such as shown in FIGS. 1–8 and in a size wherein the height of the insert is increased by 0.10 inch. Further, as shown in FIGS. 9 and 10, the insert, in addition to the standard form is made for elevation to the left as shown at 14' in FIG. 9 and elevation to the right as shown at 14" in FIG. 10. In each of the FIGS. 9 and 10 forms of the invention, the elevation amounts to 3.5° as indicated.

The different height and the elevated left and right tibial inserts are employed to provide flexibility during implanting procedure so that the surgeon has the opportunity to make final adjustments after the tibial and femoral components have been cemented to their respective bones.

The following is a listing of various dimensions of a knee joint prothesis for an adult male of approximately average height of about 70 inches.

TIBIAL COMPONENT

Overall length of component 3.9 inches. Length of stem 3.5 inches. Width of the table 2.625 inches. Depth of the table 1.90 inches. Material of construction: Vitallium.

UNIVERSAL TIBIAL INSERT

Radius of spherical depression 1 inch. Overall thickness of the insert 0.5 inch. Height of insert from the top surface to the edge of the flange recesses 0.2 inch. Material of construction: high density polyethylene.

FEMORAL COMPONENT

Overall length 3.5 inches. Length of stem 3 inches. Radius of the sphere 1 inch. Radius of curvature of shoulder portions 78 and 76– 0.7 inch. Overall width of component 2.65 inches. Height of front flange 2 inches. Material of construction: Vitallium.

The procedure for implanting the prosthesis generally comprises removal of the curiate ligaments; removing a small portion of the top of the tibia; removing a small portion of the lower end of the femur; boring the tibia and femur for receipt of the stem portions of their respective components; cementing the components to their respective bones and thereafter slideably inserting and pin connecting the tibial insert of the appropriate size and configuration to the table of the tibial component.

From the foregoing description of the present invention, it will be seen that the objects and advantages hereinbefore set forth and others are fully accomplished.

We claim:

1. A knee joint prosthesis comprising a tibial component; a tibial component insert; and a femoral component; said tibial component comprising an anchoring stem portion, one end of said stem portion adapted to be received in a longitudinal bore in a patient's tibia, the other end of said stem portion being integral with a table, the top surface of which is generally normal to the stem portion and having lateral edge flanges.

said tibial component insert comprising a plate shaped to be received on the tibial component table in locking engagement with the table edge flanges and the upper surface thereof having a centrally positioned spheroidal depression surrounded by a plane surface;

said femoral component comprising a stem, one end of said stem adapted to be received in a longitudinal bore in a patient's femur, the other end of said stem being integral with a depending generally spheroidal surface having generally the same radius as the radius of the spheroidal depression in said insert, said spheroidal surface having lateral shoulders each of which has a flat surface which engages the plane surface of the insert when the stems of the tibial and femoral components are in longitudinal alignment and a generally cylindrical surface having a radius of curvature about the axis of pivotal motion of the spheroidal surface with the spheroidal depression to permit rearward swing motion of the tibial component relative to the femoral component and relative axial rotation of said components.

2. The invention defined in claim 1 wherein the tibial and femoral components comprise a cobalt-chromium alloy and the tibial insert comprises plastic.

3. The invention defined in claim 1 wherein the femoral component includes an upstanding flange adapted to form a seat for the knee cap.

4. The invention defined in claim 1 wherein the edge flanges of the table of said tibial component are tapered inwardly from the front to the rear, grooves are provided in the tibial component insert and are correspondingly tapered.

5. The invention defined in claim 1 including an opening in the central portion of the spheroidal depression of said tibial component.

6. The invention defined in claim 1 further characterized in that said tibial component insert is of a thickness such that the length of the leg containing the prosthesis is the same as the length of the other leg of the patient.

7. The invention defined in claim 1 further characterized in that said tibial component insert is elevated to the left.

8. The invention defined in claim 1 further characterized in that said tibial component insert is elevated to the right.

* * * * *